United States Patent [19]
Gilmore et al.

[11] Patent Number: 5,249,456
[45] Date of Patent: Oct. 5, 1993

[54] ASSEMBLY SUITABLE FOR DETERMINING A COEFFICIENT OF MOISTURE EXPANSION OF A WORKPIECE

[75] Inventors: James F. Gilmore, Rochester; Carl A. Lloyd, Bloomfield, both of N.Y.

[73] Assignee: Eastman Kodak Company, Rochester, N.Y.

[21] Appl. No.: 904,747

[22] Filed: Jun. 26, 1992

[51] Int. Cl.5 .................. G01G 21/23; G01N 25/00
[52] U.S. Cl. .................................. 73/73; 177/245; 374/14
[58] Field of Search .............. 73/73, 76; 374/55, 52, 374/14; 177/245

[56] References Cited
U.S. PATENT DOCUMENTS 2,886,967  5/1959  Conti ............................ 73/73 X
3,055,206  9/1962  Watson et al. ................. 73/76 X
3,172,493  3/1965  Von Koch et al. ............. 73/76 X
4,923,307  5/1990  Gilmore et al. .............. 374/56 X
4,924,477  5/1990  Gilmore et al. .................. 374/55
4,964,734  10/1990  Yoshida et al. ................. 374/14

Primary Examiner—Daniel M. Yasich
Attorney, Agent, or Firm—Kevin A. Sembrat

[57] ABSTRACT

An assembly for determining a coefficient of moisture expansion of a single, identified workpiece or coupon. The assembly includes means for positioning the workpiece in a chamber having known environmental parameters; means for determining a workpiece length change, $\Delta L$ caused by a chamber induced change in the workpiece's moisture content $\Delta M$; and, means for measuring a chamber-induced change in the workpiece's moisture content $\Delta M$.

5 Claims, 3 Drawing Sheets

ASSEMBLY SUITABLE FOR DETERMINING A COEFFICIENT OF MOISTURE EXPANSION OF A WORKPIECE

BACKGROUND OF THE INVENTION

This invention relates to a method and an assembly suitable for precisely determining a coefficient of moisture expansion of a workpiece.

INTRODUCTION TO THE INVENTION

The coefficient of moisture expansion (CME) of a workpiece can provide a measure of a length deformation $\Delta L$ induced in a workpiece by an amount of moisture $\Delta M$ that it may absorb/release. The CME may be expressed by an equation (1):

$$CME = \frac{\Delta L}{L \Delta M} \quad (1)$$

where,
- L = length of a workpiece having a uniform thermal strain;
- $\Delta L$ = a linear deformation due to a change in moisture; and
- $\Delta M$ = absorbed/released moisture.

It is important to know the coefficient of moisture expansion, for example, when a workpiece is part of a statically indeterminate system. Here, expansions or contractions $\Delta L$ of the workpiece, induced by a change in moisture $\Delta M$, may be inhibited or entirely prevented in certain directions. This, in turn, may cause significant stresses in the system, which stresses may have to be investigated by way of the coefficient of moisture expansion, and concomitantly accommodated by the system.

SUMMARY OF THE INVENTION

Our motivation for providing a novel method and assembly suitable for precisely determining the CME of a workpiece, comes about in the following way.

We are working with workpieces that comprise novel compositions; that may be utilized in systems of exceptional sensitivity and high performance; and, which may be subjected to unusual moisture gradients $\Delta M$. For example, the workpiece may comprise a composite i.e., a non-homogenous graphite/epoxy composite which comprises a critical component of an optics device that is mounted in a spacecraft.

To an end of designing the workpiece to ensure a desired system performance, we determine its coefficient of moisture expansion. The CME's of our workpieces typically define a range of values e.g., from 100.00 $\mu$inch/inch % M $\pm$ 10.00 to 300.00 $\mu$inch/inch % M $\pm$ 10.00. As indicated therefore, a required precision of the CME computation is approximately 10 $\mu$inch/inch % M.

Attention is now directed to FIG. 1A, which shows one typical and important test facility 10 that may be used in determining the CME of a workpiece. Our strategy in disclosing this typical test facility 10 is three-fold: to make explicit heretofore hidden assumptions about a typical testing methodology; to show that purblindness to these hidden assumptions can vitiate or thwart a desired precision of measurement; and, to help point the way to the novel assembly of the present invention which makes explicit these hidden assumptions and defines a new high precision CME testing assembly.

Canonical elements of the FIG. 1A test facility 10 include first and second coupons 12, 14 of known length L, and derivatives of a workpiece (not shown) whose CME is to be discerned by way of the coupons 12, 14.

The first coupon 12 is attached at one end to a conventional linear variable differential transformer 16 (LVDT). The LVDT 16 comprises a transformer probe rod or core connected to the coupon 12. In response to moisture expansions/contractions of the coupon 12, the resultant displacements $\Delta L$ of the coupon 12 may be transmitted to the LVDT transformer. This last action, in turn, can convert the displacement $\Delta L$ into a proportional voltage signal, which can be routinely converted into the parameter $\Delta L$ of equation (1), supra.

Canonical elements of the FIG. 1A test facility 10 also include the second coupon 14 connected to a conventional scale 18. The scale 18 can monitor weight gains/losses of the second coupon 14, thereby providing the second required parameter for computation of equation (1), supra, namely, $\Delta M$.

We now make explicit heretofore hidden or not recognized assumptions about the CME methodology realized by way of the FIG. 1A test facility 10. To this end, we also direct attention to FIG. 1B, which comprises our addition to FIG. 1A, and which includes a demarcation of "environmental zones" 20 and 22. In particular, the environmental zone 20 surrounds the first coupon 12, and the environmental zone 22 surrounds the second coupon 14.

Crucial hidden or not recognized assumptions about the FIG. 1 CME methodology include the following points: that the first coupon 12 is absolutely identical with the second coupon 14, and that the coupons 12, 14 share a unique, common testing environment. There is an implicit assumption that the coupons 12, 14 share attributes of "identicality" and "commonality", so that by way of "juxtaposition", two independent measurements $\Delta L$, $\Delta M$, may be inputted to one CME equation, namely, equation (1), supra, thereby determining a precision of measurement.

We now show that the assumptions of identicality and commonality may be untenable, thereby thwarting the obtainment of a required degree of precision.

As to identicality, first recall that the coupons 12, 14 may comprise composite, non-homogenous materials, like graphite/epoxy. We have discovered that the non-homogenity of the coupons 12, 14 can manifest itself several fold, so that the coupons 12, 14 may have a qualitatively different fiber volume, percentage of microcracking, and/or void content. Since these parameters may be directly correlated to a different moisture content, the differences of these parameters from coupon 12 to coupon 14, may directly work to undermine the assumption of identicality. These differences, in turn, can effect an inherent precision of the CME computation.

Moreover, we have discovered that the coupons 12, 14 may define qualitatively different boundary conditions, and have qualitatively different thicknesses, perimeters/lengths, and/or cross-sectional areas. Again, since these last parameters may be directly correlated to a differential moisture content, the difference of these parameters from coupon 12 to coupon 14 may directly work to undermine the assumption of identicality. The loss of identicality, in turn, can effect an inherent precision of the CME computation.

As to commonality, we have discovered that the environmental zones 20 and 22 that are dedicated to each of the two coupons 12, 14 may be qualitatively different. This is because the two environmental zones 20 and 22 may have a different moisture content, or a different temperature, or respond differently to external shocks or perturbations. Since the differences in the two environmental zones 20 and 22 may abrogate the implicit assumption of commonality of environment, a unique basis for combining the independent parameters $\Delta L$, $\Delta M$ into a common CME equation, may be undermined, thereby resulting in a loss of computation precision.

In summary, we have discovered that some important and typical CME methodologies have assumed (or been non-cognizant) of the points of presumed identicality of coupons, and their presumed commonality of testing environment. The consequences of this situation can manifest themselves in a loss of CME precision. As alluded to above, our exposure and critique of the axiomatic assumptions underlying these CME methodologies, helps point the way to the novel method and assembly of the present invention, which makes explicit these assumptions and defines a new high precision CME assembly.

Applicants hereinbelow describe an assembly suitable for determining a coefficient of moisture expansion of a single, identified workpiece, comprising:

(1) a chamber for maintaining said workpiece in a known environment;

(2) a first linear variable differential transformer containing a coil and a central core;

(3) a second linear variable differential transformer containing a coil and a central core;

(4) a weighing means; and (5) means for positioning said workpiece in the chamber comprising means for connecting one end of said workpiece through the core of the first linear variable differential transformer to said weighing means and an opposite end of said workpiece to the core of the second linear variable differential transformer, such that a moisture-induced length value change $\Delta L$ of said workpiece may be determined by utilizing said first and second linear variable differential transformers; and such that a chamber-induced change in moisture content value $\Delta M$ of said workpiece may be determined by utilizing said weighing means.

An important advantage of the novel assembly is that it can provide computations of the CME equation that have an exceptionally precise magnitude. For example, the CME computations of our workpieces comprising a graphite/epoxy composite may be 100.00 $\mu$inch/inch % M±10.00, thereby realizing a precision of at least 5 times, for example, 10 times greater than extant CME computation test facilities.

The inventors realize this significant advantage by exposing the hidden and false assumptions underlying extent methodologies, namely, an employment of two coupons implicitly presumed to be identical and to be tested within a common environment, and jettisoning the two coupon approach in favor of a one coupon testing assembly: the one coupon, by definition, obliged to be identical to itself and to be tested in only one environment.

BRIEF DESCRIPTION OF THE DRAWING

The invention is illustrated in the accompanying drawing, in which.

DETAILED DESCRIPTION AND PREFERRED EMBODIMENT OF THE INVENTION

Figure 1A:
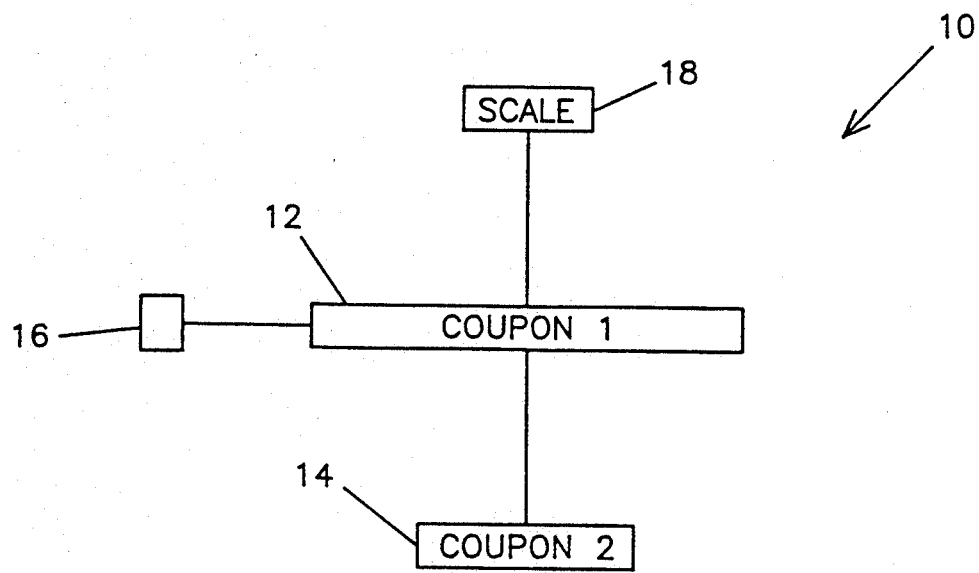
FIG. 1A shows a typical CME test facility.
Figure 1B:
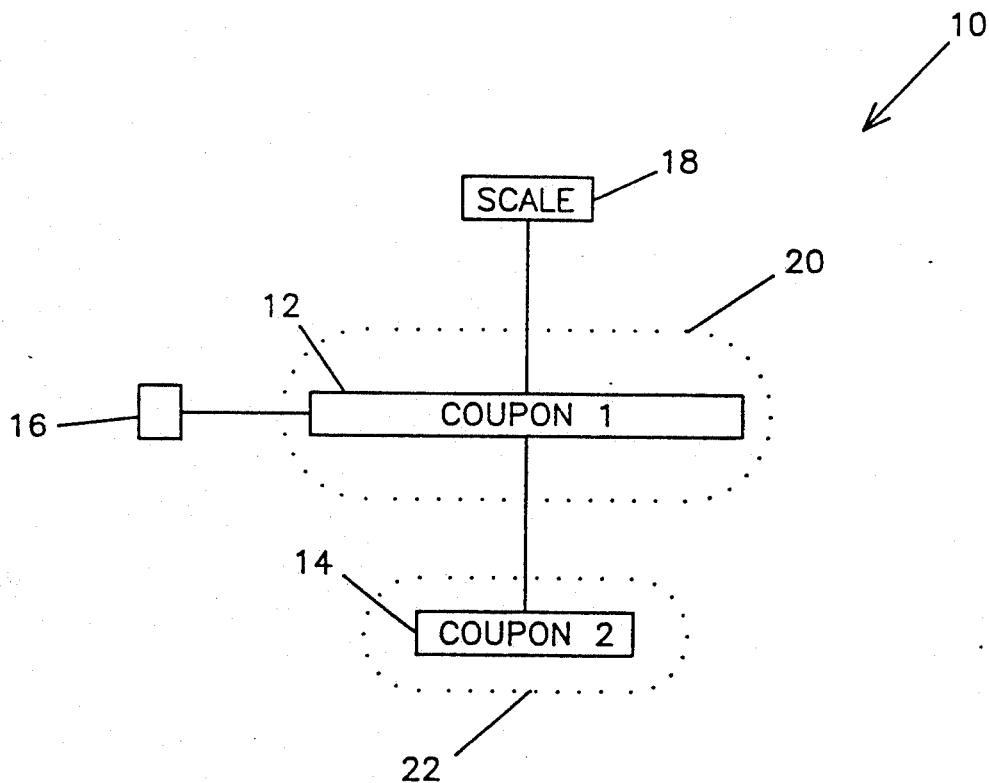
FIG. 1B shows the FIG. 1A CME test facility supplemented by inventor defined environmental zones.
Figure 2A:
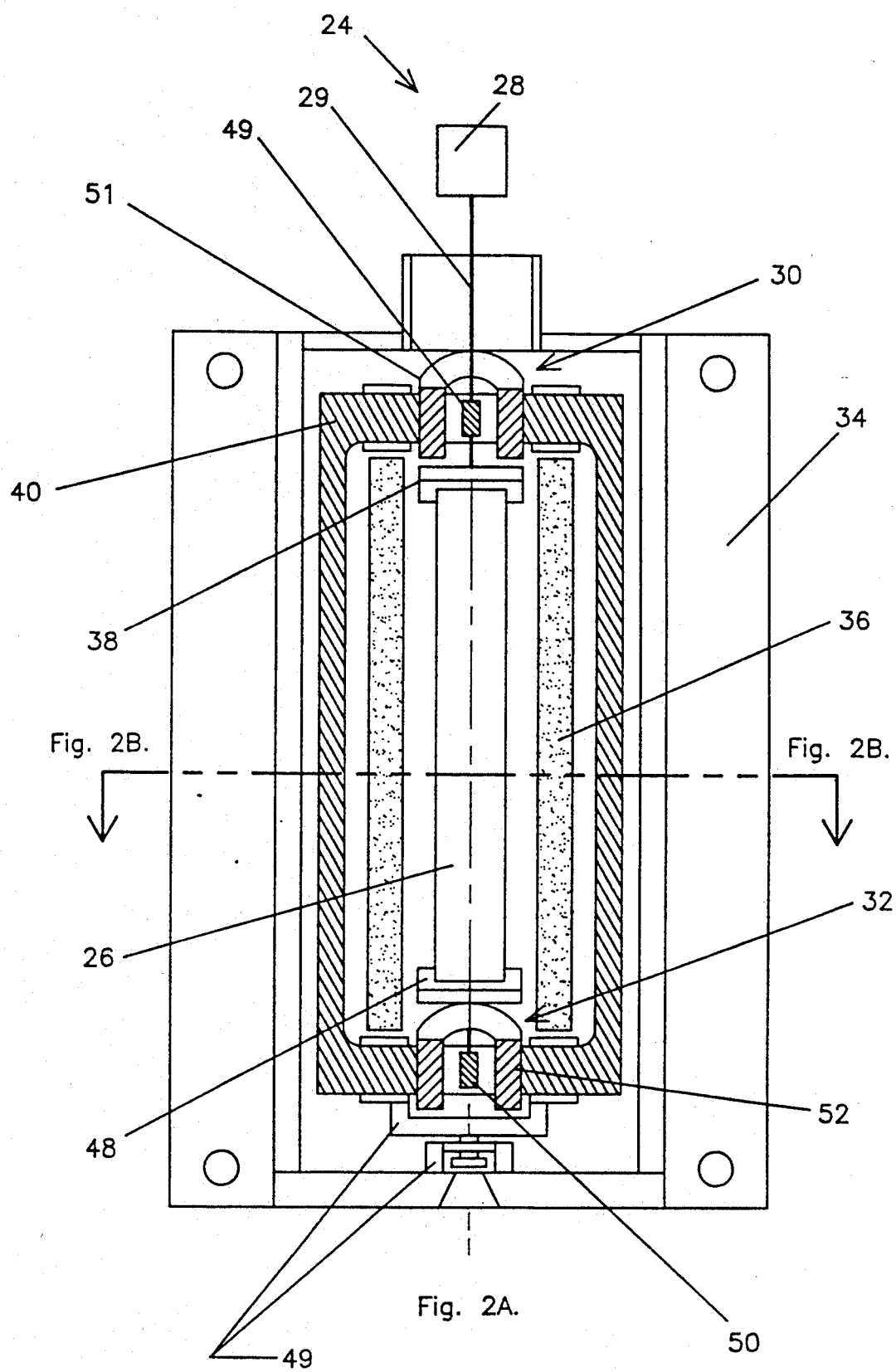
FIGS. 2A and 2B show front and plan cross-sectional views respectively of a novel CME test assembly.
Figure 2B:
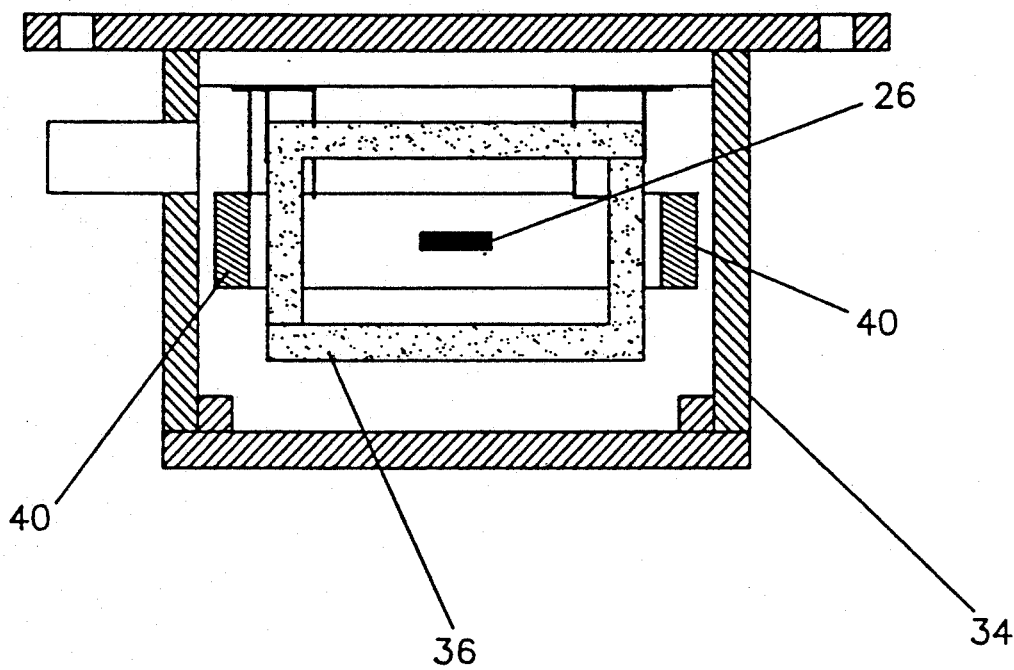

Attention is now directed to FIGS. 2A and 2B which show front and plan views respectively of a CME test assembly 24 suitable for realizing the novel CME method of the present invention.

In overview, the FIGS. 2A and 2B CME test assembly 24 suspends one workpiece (coupon) 26 from a high precision scale 28 via wire 29, in order to precisely measure the workpiece 26 weight (i.e., $\Delta M$). Preferably, at the same time, two opposing linear variable differential transformers 30, 32 (LVDT) attached to opposite ends of the same workpiece 26, precisely measure its length changes $\Delta L$. One can correlate the $\Delta L$ and $\Delta M$ values in one CME equation (CME=$\Delta L/L\Delta M$) without derogation of precision, since the data is derived from a single, identified workpiece bounded by one environmental zone.

The FIGS. 2A and 2B CME test assembly 24 preferably includes a conventional thermal vacuum chamber 34 that can establish and maintain known environmental parameters, for example, temperature, relative humidity, pressure. The chamber 34 preferably comprises aluminum, in order to readily conduct heat and to provide a uniform temperature gradient, and is preferably insulated to help stabilize the chamber 34 temperature. The chamber 34 may alternatively comprise copper, invar or steel. The chamber 34 preferably is positioned on an isolation table, not shown, in order to minimize external pertubations and to provide a stable environment for the workpiece 26.

Preferably included in the chamber 34, and surrounding the workpiece 26, is a conventional high conductivity insulated thermal shroud 36. The thermal shroud 36 can heat and cool the workpiece 26, via external hot and cold water reservoirs, not shown, and can function to provide an optimum heat exchange capability to precisely define the environmental parameters of the workpiece 26.

The thermal shroud 36 may enclose the first and second linear variable differential transformers 30, 32, the latter attached to opposite ends of the workpiece 26, or as shown in FIG. 2A, the LVDT's 30, 32 may preferably be outside the thermal shroud 36. LVDTs' cores (49, 50) are preferably attached to opposing ends of the workpiece 26 via sample support assemblies 39 and 48. The unique sample supports 38 preferably comprise ball and socket positioners to locate the sides of the workpiece 26, and spring loaded axial positioners to maintain LVDT core and workpiece 26 contact. Further, the LVDT coils (51, 52) are preferably housed in a low conductivity and low coefficient of thermal expansion reference structure 40. In addition, the reference structure contains a preset calibration adjustment screw and brackets 49. The LVDT's 30, 32 function in opposition, so that a required CME parameter $\Delta L$ may be determined in accordance with an equation (2):

$$\Delta L = |LVDT_{30}(L) - LVDT_{32}(L)| \qquad (2).$$

An important advantage of the employment of opposing LVDT's is that spurious electronic drift and vibration signals may be significantly attenuated.

Preferably, the determination of the CME parameter $\Delta L$ is obtained simultaneously with a determination of the CME parameter $\Delta M$. The last parameter, $\Delta M$, may be obtained via the high precision scale 28 that is attached to the workpiece 26 via wire 29.

The parameters $\Delta L$, $\Delta M$ are preferably input to a data acquisition system, for example, a Hewlett Packard Model 86B personal computer, programmed to compute a high precision CME value in accordance with the equation $CME = \Delta L / L \Delta M$.

What is claimed:

1. An assembly suitable for determining a coefficient of moisture expansion of a single, identified workpiece, comprising:
    (1) a chamber for maintaining said workpiece in a known environment;
    (2) a first linear variable differential transformer containing a coil and a central core;
    (3) a second linear variable differential transformer containing a coil and a central core;
    (4) a weighing means; and
    (5) means for positioning said workpiece in the chamber comprising means for connecting one end of said workpiece through the core of the first linear variable differential transformer to said weighing means and an opposite end of said workpiece to the core of the second linear variable differential transformer, such that a moisture-induced length change value $\Delta L$ of said workpiece may be determined by utilizing said first and second linear variable differential transformers; and such that a chamber-induced change in moisture content value $\Delta M$ of said workpiece may be determined by utilizing said weighing means.

2. An assembly according to claim 1, wherein said chamber comprises a thermal vacuum chamber for providing a uniform temperature.

3. An assembly according to claim 1, wherein said weighing means comprises a precision scale.

4. An assembly according to claim 1, wherein said assembly further comprises a thermal shroud surrounding said workpiece, for heating and cooling said workpiece.

5. An assembly according to claim 1, wherein said workpiece's $\Delta L$ and $\Delta M$ values may be determined essentially simultaneously.

* * * * *